United States Patent
Warren

(10) Patent No.: US 8,925,550 B2
(45) Date of Patent: Jan. 6, 2015

(54) SINGLE SIDED MODULAR OXYGEN CANNULA AND GAS/AIR DELIVERY SYSTEM

(71) Applicant: Sydney A Warren, Los Angeles, CA (US)

(72) Inventor: Sydney A Warren, Los Angeles, CA (US)

( * ) Notice: Subject to any disclaimer, the term of this patent is extended or adjusted under 35 U.S.C. 154(b) by 0 days.

(21) Appl. No.: 13/787,348

(22) Filed: Mar. 6, 2013

(65) Prior Publication Data
US 2014/0251323 A1 Sep. 11, 2014

(51) Int. Cl.

| | |
|---|---|
| A61M 15/08 | (2006.01) |
| A62B 7/00 | (2006.01) |
| A62B 18/08 | (2006.01) |
| A62B 9/04 | (2006.01) |
| A61M 16/00 | (2006.01) |
| A61M 16/04 | (2006.01) |
| A61M 16/06 | (2006.01) |
| A61M 16/08 | (2006.01) |
| A61M 16/10 | (2006.01) |
| A61M 16/12 | (2006.01) |

(52) U.S. Cl.
CPC ....... *A61M 16/0057* (2013.01); *A61M 16/0488* (2013.01); *A61M 16/0666* (2013.01); *A61M 16/0683* (2013.01); *A61M 16/0875* (2013.01); *A61M 16/105* (2013.01); *A61M 16/12* (2013.01)
USPC ............. 128/207.18; 128/206.27; 128/202.27

(58) Field of Classification Search
USPC ............. 128/200.24, 202.13, 204.18, 206.21, 128/206.27–206.29, 207.11, 206.11, 128/207.13, 207.18; 381/370, 374, 377, 381/378, 381–383; 403/119, 161–165
See application file for complete search history.

(56) References Cited

U.S. PATENT DOCUMENTS

| | | | |
|---|---|---|---|
| 4,465,067 A | 8/1984 | Koch et al. | |
| 4,996,983 A | 3/1991 | AmRhein | |
| 5,193,534 A | 3/1993 | Peppler | |
| 5,582,164 A | 12/1996 | Sanders | |
| 5,613,222 A * | 3/1997 | Guenther | 455/575.2 |
| 5,803,063 A | 9/1998 | Corey | |
| 6,065,473 A | 5/2000 | McCombs | |
| 6,220,244 B1 | 4/2001 | McLaughlin | |
| 6,247,470 B1 | 6/2001 | Ketchedjian | |

(Continued)

FOREIGN PATENT DOCUMENTS

| | | |
|---|---|---|
| WO | 0054854 | 9/2000 |
| WO | 2005097018 | 10/2005 |
| WO | 2007028877 | 3/2007 |

OTHER PUBLICATIONS

Southmetic OxyArm web pages.

*Primary Examiner* — Kristen Matter
(74) *Attorney, Agent, or Firm* — Kirk A. Buhler; Buhler & Associates

(57) ABSTRACT

A retainer for a single-sided modular cannula portable gas delivery system to secure a mouthpiece or nosepiece, a gas delivery pack and a single-sided modular medical cannula tubing assembly. An over-the ear secured modular mounting sleeve having an elongated central semi-circular cavity for securing a nasal cannula. A pair of engaged discs allow the cavity to rotate. The pair of discs have a plurality of elevated ridges that lock the semi-circular cavity in angular relationship to the ear piece. The ear piece has a malleable metal insert that is located at least partially within the ear piece that allows the ear piece to be bent for comfort.

10 Claims, 15 Drawing Sheets

(56) References Cited

U.S. PATENT DOCUMENTS

| | | |
|---|---|---|
| D449,883 S | 10/2001 | McDonald |
| 6,450,166 B1 | 9/2002 | McDonald |
| 6,470,885 B1 | 10/2002 | Blue |
| 6,495,207 B1 | 12/2002 | Prociw et al. |
| 6,510,859 B1 | 1/2003 | Kamikawa |
| 6,526,968 B1 | 3/2003 | Izuchukwu et al. |
| 6,595,207 B1 | 7/2003 | McDonald et al. |
| 6,619,288 B2 | 9/2003 | Demers |
| 6,631,719 B2 | 10/2003 | McDonald et al. |
| 6,675,796 B2 | 1/2004 | McDonald |
| 6,691,706 B2 | 2/2004 | Ives |
| D515,697 S | 2/2006 | Nakamura |
| D533,656 S | 12/2006 | Taylor |
| 7,694,680 B2 * | 4/2010 | Brichetto ............... 128/206.12 |
| 2006/0042631 A1 | 3/2006 | Martin |
| 2008/0049960 A1 | 2/2008 | Petersen |
| 2008/0053457 A1 * | 3/2008 | McDonald ............ 128/207.17 |
| 2008/0223369 A1 * | 9/2008 | Warren .................. 128/205.25 |
| 2009/0000618 A1 * | 1/2009 | Warren .................. 128/202.13 |

\* cited by examiner

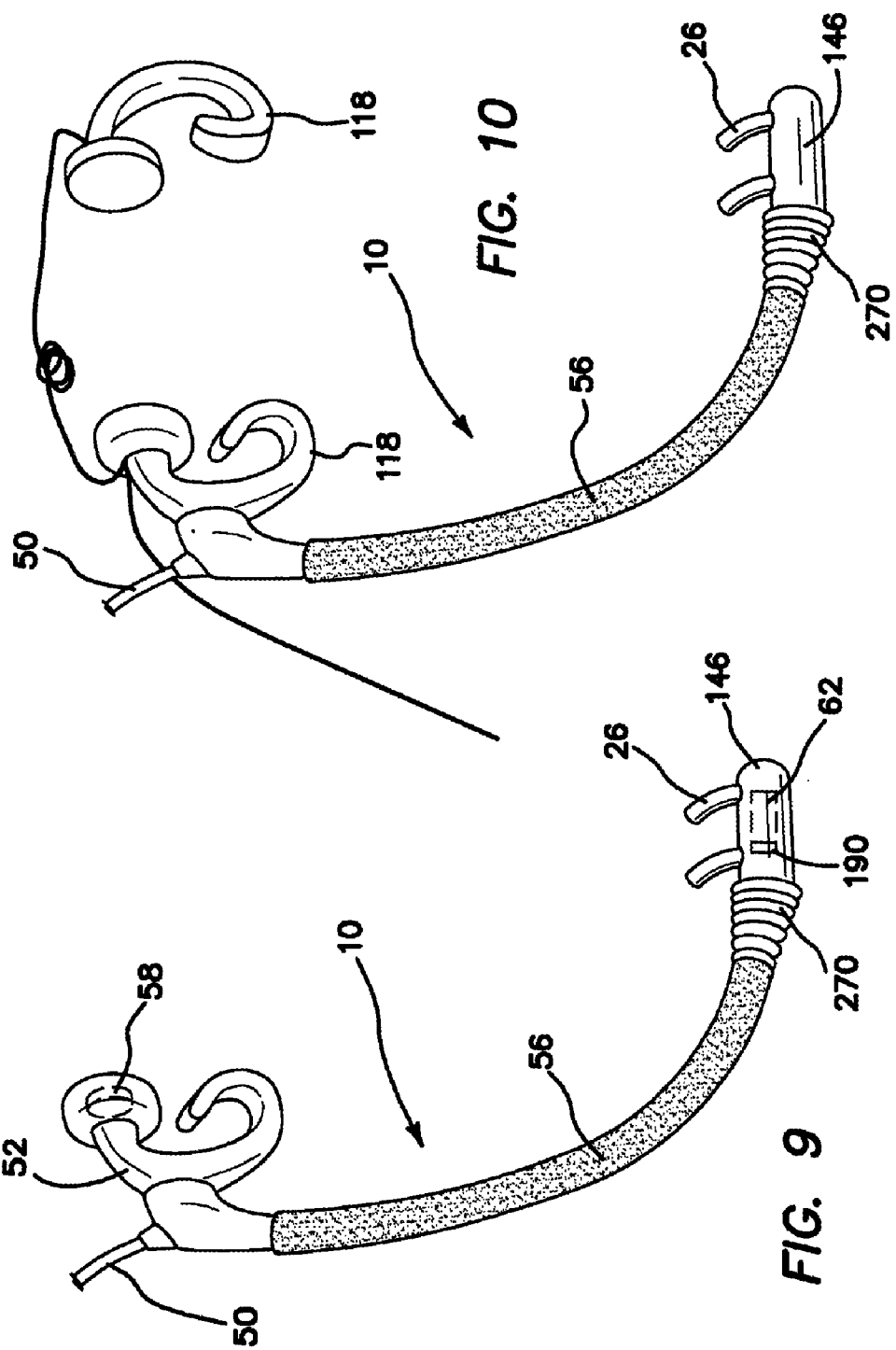

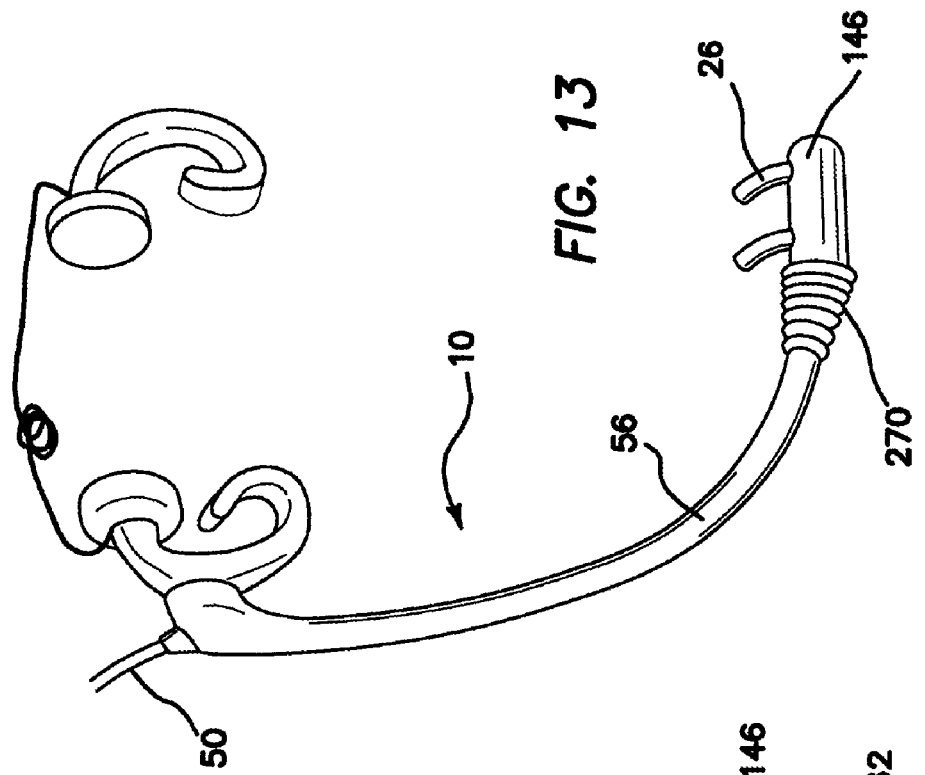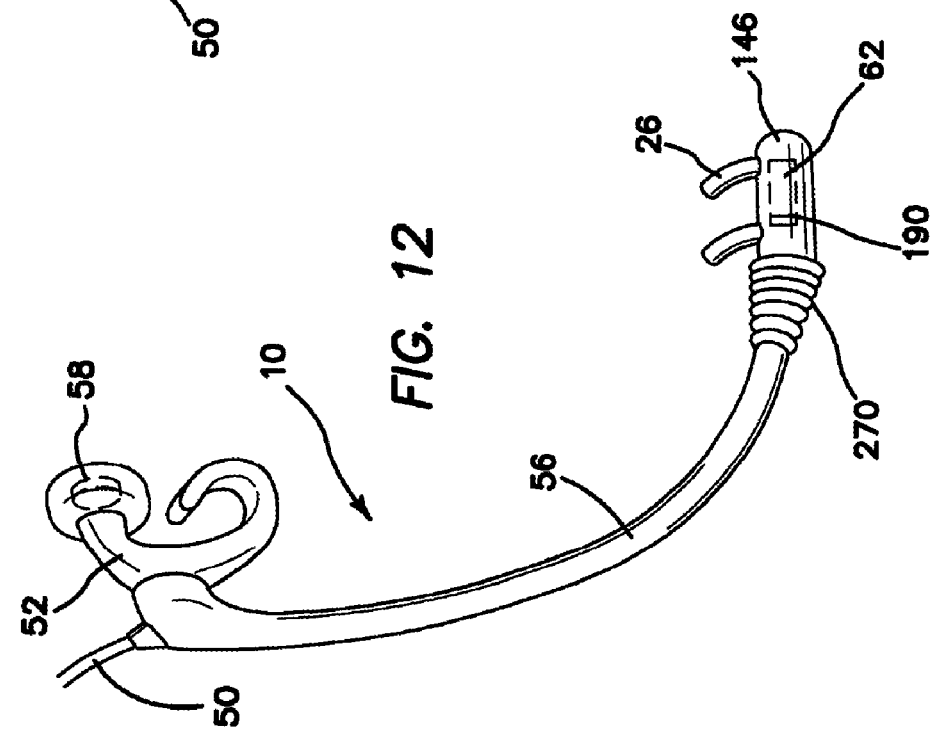

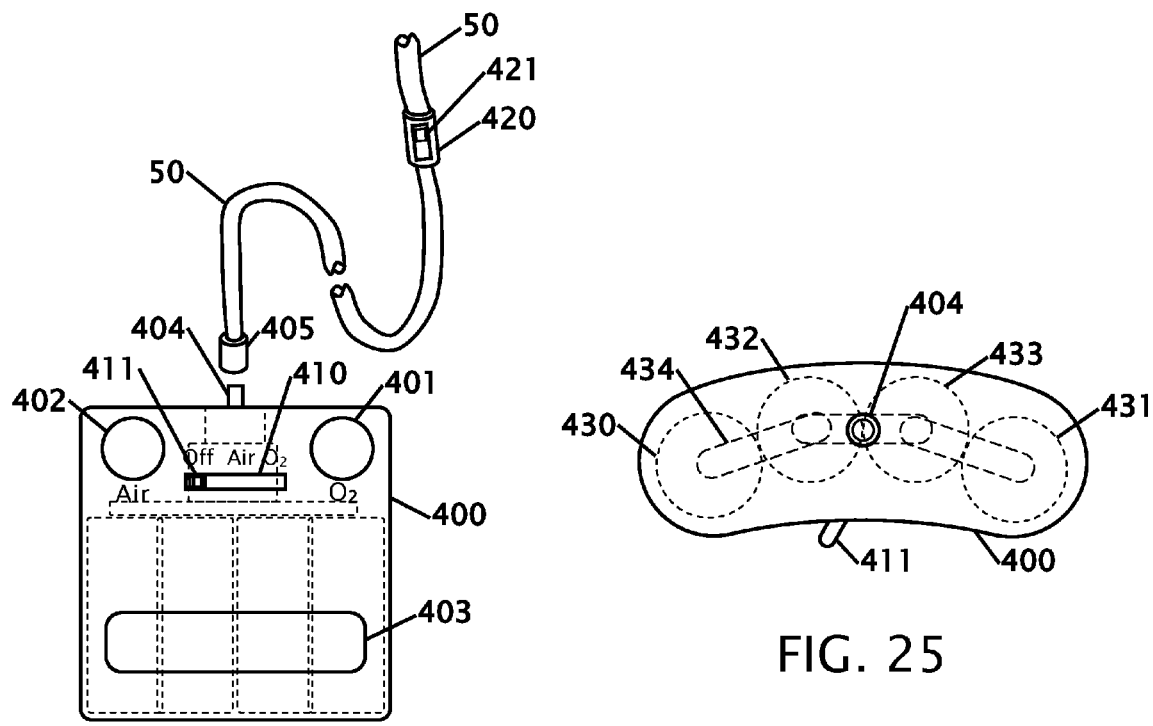
FIG. 24
FIG. 25
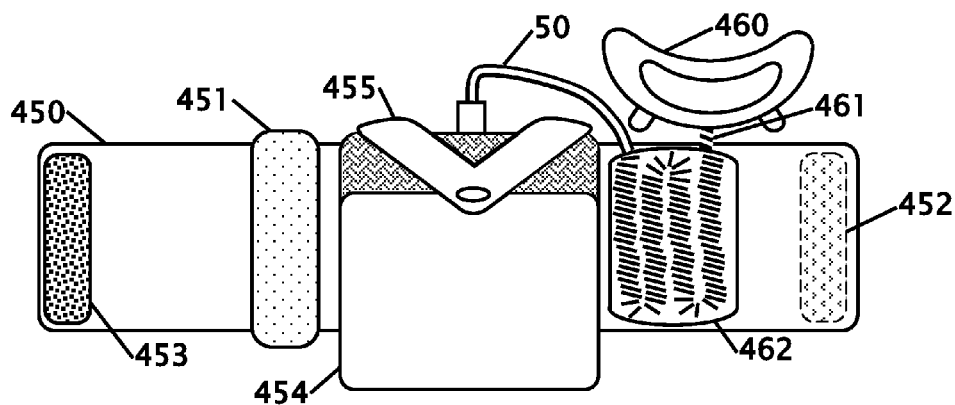
FIG. 26

SINGLE SIDED MODULAR OXYGEN CANNULA AND GAS/AIR DELIVERY SYSTEM

CROSS REFERENCE TO RELATED APPLICATION

This application is a continuation-in-part of applicant's co-pending application Ser. No. 12/204,682 filed Sep. 4, 2008 which is a continuation-in-part of U.S. divisional application Ser. No. 12/131,746, filed Jun. 2, 2008, which is a divisional application of U.S. application Ser. No. 10/945,546 filed Sep. 20, 2004.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention relates generally to a single-sided modular cannula system for delivering oxygen and/or filtered air. More particularly, the invention relates to a single-sided modular portable system for delivering oxygen and/or filtered air to persons in a comfortable and convenient manner while providing additional options for use in combination with telecommunications and audio devices.

2. Description of Related Art including information disclosed under 37 CFR 1.97 and 1.98

Clean air is an important part of maintaining health in an otherwise healthy person. Environments that contain airborne pollutants and infectious agents have received much publicity and awareness. Second hand cigarette smoke, carbon monoxide, SARS, dust, pollen and car exhaust, among other such pollutants can cause respiratory discomfort, damage or inefficiency.

Some of these effects can be temporary, as when exposed to an allergen where the effect disappears when the allergen is removed, and some of these effects can be permanent, as when second-hand cigarette smoke causes cancer. It is beneficial to an otherwise healthy person to maintain a high quality supply of breathable air by either filtering the ambient air before inhalation, or providing an alternate source for the breathable air that excludes a large fraction of the ambient air.

This effect is well known for unhealthy people, such as an emphysema patient who pulls a cart with an oxygen tank that supplies oxygen to an area around the nose or mouth to enhance the oxygen uptake of damaged lungs. Another example is the oxygen masks used in hospitals to provide a similar effect for the same or other medical purpose. These systems provide higher quality air in a manner that is not easily portable for an individual, and certainly not designed to be fashionable or attractive.

A personal oxygen and/or filtered air delivery system must further meet certain functional requirements. It must be able to remove some potentially, perceived or actually harmful fraction of the ambient air, or must be able to provide at least a portion of the inhaled air by displacing at least a portion, if not all, of the ambient air with either air filtered by an air filtration pump, or air from a compressed gas tank of appropriate dimension so as to be worn on the body. In the alternative it may be required to do both functions, with some portion of the inhaled air coming through the filter, some portion coming from the gas tank, and the remaining air, if any, coming from the ambient air.

For the purposes of this application, higher quality air refers to air with either more desirable characteristics, air which has fewer undesirable characteristics or air which has both more desirable or fewer undesirable characteristics. Percent O2 content, pollen, particles, aromatic compounds, gaseous and particulate carbon compounds including hydrocarbons, nitrogen containing compounds, carbon monoxide, ozone, viral infectious agents, bacterial infectious agents, sulfur containing compounds, dust, soot, smoke, smog, and many other compounds can, among many other factors, be factors used when determining characteristics of air quality. Desirable and undesirable characteristics can be left to the objective determination of government and industry agencies or subjective determination of each individual user of this system.

As air quality in some cities declines, and as the perception that the number and quantity of harmful components in the air is increasing, there is a growing group of people who wish to breath higher quality air but are unwilling to pull a tank of higher quality air around in a cart, or unwilling to wear a standard mask or nose-piece normally associated with an unhealthy person, and thus convey a negative body image to others or to themselves.

Further, there has developed a desire by some people to stop periodically in commercial locations called oxygen bars, or commercial locations, like health clubs, that offer oxygen bars in addition to other services. These commercial locations provide customers with, among other services, an opportunity to temporarily inhale breathable air that can contain higher concentrations of oxygen.

Such breathable air may also be enhanced with aromas pleasing to the customer. Currently these customers use a small flexible hose called a cannula to deliver the oxygen enriched breathable air into their nostrils. As part of the experience of being in an oxygen bar and social setting, it is desirable to portray the experience as glamorous or fashionable in addition to being functional.

Accordingly, it is desirable for the cannula to be incorporated into other devices normally appearing on or around the face of a person to enhance the appearance of the medical oxygen user, or to discretely disguise the functional aspect of the cannula.

Various single-sided modular embodiments of the present invention are directed to addressing various needs in connection with ensuring that higher quality air and/or oxygen is delivered to the nose and or mouth area of a person wearing the system disclosed in this invention. These various embodiments encourage those who need oxygen to be as active and socially engaging as they were previous to being prescribed medical oxygen. These single-sided modular options attaches the oxygen and/or filtered air delivery system via proprietary adaptors to either an ear-piece, aviators telecommunications headset, helmet, cap, visor or hats, as well as to the frame of eye glasses.

As people feel the need to maintain communications in a near constant manner, they often make use of portable wireless earpieces. In a similar manner, many people choose to take advantage of compact headphones for use with personal music systems. The combination of these devices with oxygen/air breathing devices represents new flexibility and freedom for those who desire to take advantage of both systems in a comfortable and convenient manner.

Various patents address systems that are designed to permit the wearer to breathe oxygen or purified air. Sanders, U.S. Pat. No. 5,582,164, disclose a portable gas delivery system that includes a gas storage assembly that is connected to a nose piece using flexible tubing. The gas storage assembly includes a strap that enables it to be readily carried by the person using this system.

AmRhein, U.S. Pat. No. 4,996,983, discusses a portable oxygen delivery system in which gas storage containers are incorporated into the temples on eyeglasses. Air delivery tubes extend around the wearer's ears to a nose piece, prongs or portal that is placed in the wearer's nose.

Peppler, U.S. Pat. No. 5,193,534; and Timmons et al., U.S. Pat. No. 4,559,941, both describe incorporating an oxygen delivery system into eyeglasses. The oxygen is delivered from a storage container to the temples on the eyeglasses. The oxygen is then routed to a nosepiece through the eyeglasses.

Koch et al., U.S. Pat. No. 4,465,067, discloses a system for delivering oxygen. This system has a configuration that is similar to eyeglasses except that it does not include any lenses. Oxygen is delivered to the temple portion that wraps around the wearer's ear and then to a nose piece that is positioned proximate the wearer's nose.

Izuchukwu et al., U.S. Pat. No. 6,526,968, discusses an air delivery system that is incorporated into a utility belt that is worn by the user. The utility belt includes a pack for storing the compressed gas and a port for connecting to a mask using flexible tubing.

Izuchukwu et al., U.S. Pat. No. 6,510,859, discloses an emergency breathing apparatus that includes a hood, which is placed over the user's entire head. Air is delivered to the hood from a storage pack. While such a system is acceptable for emergency situations, the fact that it covers the user's entire head limits the ability for the user to perform many activities while wearing this device.

McDonald, et al., U.S. Pat. No. 6,595,207, describes an oxygen diffuser for a lightweight oxygen delivery system for a patient, the oxygen delivery system being of the type comprising a mount for seated engagement on a patient's head or ear, an elongated tubular boom for oxygen delivery secured at one end to the mount and having the diffuser secured to the other end, the diffuser to deliver oxygen passed through the boom to a space in the vicinity of the patient's nose and mouth, the diffuser comprising a body having a wall, the interior surface of which wall is of generally concave configuration, circumscribing a centrally positioned oxygen outlet so as to direct the flow of oxygen from the outlet generally towards the patient's nose and mouth; and a baffle seated over the oxygen outlet so as to assist in mixing of oxygen with ambient air and avoid a direct flow of oxygen towards the patient's face.

Demers, et al., U.S. Pat. No. 6,619,288, describe a breathing mask for delivering oxygen to a patient. The breathing mask has a headset for seating about the cranial region of the head of the patient, with a hollow gas delivery arm coupled to the headset. The mask also has a nosepiece that is coupled only to the hollow gas delivery arm and that delivers oxygen to the nostrils of the patient. Finally, the mask has a source of oxygen for coupling oxygen to the hollow gas delivery arm.

McCombs, et al., U.S. Pat. No. 6,065,473, describes a non-contact gas dispenser comprising a head set apparatus, a gas source and a conduit for directing the desired gas to a region proximate to the user's nose and mouth. The gas source preferably is a pressure swing adsorption apparatus that allows the user to select one of at least two pre-determined settings of product gas, each setting having a distinct concentration and flow rate different from the other setting(s).

Martin, James F. et at., U.S. Patent Application No. 2006/0042637, describes an oxygen delivery device for regulating the flow of oxygen from an oxygen source to a respiratory cannula located on the face of a patient. A host controller coupled to the oxygen delivery device accepts an input from a medical monitor relating to the blood oxygen saturation percentage of the patient. The host controller then regulates the rate of oxygen supplied to the patient based in part upon the blood oxygen saturation percentage of the patient. A high rate of oxygen is supplied to the patient when the controller detects a blood oxygen saturation level below a predetermined percentage and a low rate of oxygen is supplied when the controller detects a blood oxygen saturation level above a predetermined percentage in an order to minimize wasted oxygen.

BRIEF SUMMARY OF THE INVENTION

It is an objective of the present invention to provide a single-sided modular personal oxygen/air breathing device that is attractive, comfortable and convenient for daily wear. It is a further objective to provide such a single-sided modular cannula system that can be attached through various adapters for the constant sleeve allowing the oxygen delivery system to be used with either an ear-piece, telecommunication headsets, helmets, hats, caps, visors, masks or eye-glasses or other fashion accessories It is another objective to utilize the same single-sided modular medical cannula tubing within the universally modular sleeve to be in all hospitals around the world supplying the same safe levels of oxygen flow rates to the user's nose. It is yet another objective to provide such breathing gear that is combined with a wireless personal earpiece for use with a cellular telephone. Finally, it is an objective of the present invention to provide breathing systems that are combined with personal headphones for use with portable music players.

(1) A single-sided modular portable gas delivery system is constructed from the following components. A mouthpiece is provided that has an upper region and a lower region extending from it. The upper region includes at least one nose port and the lower region includes a mouth port. A gas delivery pack is provided that has a gas storage region, a gas compression region, a gas filtration region or a combination thereof. A single-sided modular medical cannula tubing assembly is provided that is operably attached to the mouthpiece and the gas delivery pack for delivering gas from the gas delivery pack to the mouthpiece. A single-sided modular cannula and a single-sided hollow sleeve is provided. The sleeve at least partially encloses the mouthpiece and the single-sided modular cannula tubing assembly and is adapted to attach to an ear, a hat, helmet or an eyeglass frame of a user. A wireless transceiver adapted for use with a cellular telephone is provided. The transceiver has a listening portion and a speaking portion and is attached to the sleeve assembly so as to position the listening portion adjacent a user's ear and the speaking portion adjacent a user's mouth.

(2) In a variant of the invention, the mouthpiece includes a switch for controlling flow of oxygen and air through the mouthpiece.

(5) In yet another variant, the single-sided modular cannula tubing assembly includes a least one rotatable connector adjacent the listening portion.

(6) In yet a further variant, includes at least one adapter that has a first recess and a second recess formed in it. The first recess is adapted to receive a portion of the single-sided modular cannula tubing assembly and the second recess is adapted to receive a strap for mounting the single-sided modular cannula tubing assembly with respect to a person's head.

(7) In still a further variant, a single-sided modular portable gas delivery system includes a mouthpiece that has an upper region and a lower region extending from it. The upper region includes at least one nose port and the lower region includes a mouth port. A gas delivery pack is provided that has a gas storage region, a gas compression region, a gas filtration region or a combination thereof. A single-sided modular cannula tubing assembly is provided that is operably attached to the mouthpiece and the gas delivery pack for delivering gas from the gas delivery pack to the mouthpiece. A single-sided modular cannula and a single-sided, hollow sleeve is provided. The sleeve at least partially encloses the mouthpiece and the single-sided modular cannula tubing assembly and is adapted to attach to an ear, a hat, helmet or an eyeglass frame of a user. A bracket is provided. The bracket is adapted to support a pair of headphones for use with a portable music system. The bracket is attached to the sleeve and locates the headphones in positions suitable for mounting the headphones to ears of a user.

(8) In yet a further variant, the mouthpiece includes a switch for controlling flow of oxygen and air through the mouthpiece.

(11) In yet another variant, the single-sided modular cannula tubing assembly includes a least one rotatable connector one of the headphones.

(12) In a further variant, the A single-sided modular portable gas delivery system further includes at least one adapter that has a first recess and a second recess formed therein. The first recess is adapted to receive a portion of the single-sided modular cannula tubing assembly and the second recess is adapted to receive a strap for mounting the single-sided modular cannula tubing assembly with respect to a person's head.

(13) In yet a further variant, a single-sided modular portable gas delivery system includes a gas delivery pack that has a gas storage region, a gas compression region, a gas filtration region or a combination thereof. A garment is provided that has at least one pocket, the pocket is adapted to receive the gas delivery pack. A nosepiece is provided that has at least one nose port. A single-sided modular medical cannula tubing assembly is provided that is operably attached to the nosepiece, that conceals the single-sided modular medical nasal cannula, and the gas delivery pack for delivering a flow of gas from the gas delivery pack to the nosepiece. A single-sided modular cannula and a single-sided, hollow sleeve is provided. The sleeve at least partially encloses the nosepiece, allowing the single-sided modular medical nasal cannula to protrude through the nosepiece for a snug fit into the nostrils. The single-sided modular cannula tubing assembly and is adapted to attach to an ear 66, a hat, helmet or an eyeglass frame of a user. A wireless transceiver adapted for use with a cellular telephone is provided. The transceiver has a listening portion and a speaking portion and is attached to the sleeve so as to position the listening portion adjacent a user's ear and the speaking portion adjacent a user's mouth.

(14) In still a further variant, at least one clip is provided. The clip is adapted to secure the single-sided modular medical cannula tubing assembly to the garment.

(15) In another variant of the invention, a single-sided modular portable gas delivery system includes a gas delivery pack that has a gas storage region, a gas compression region, a gas filtration region or a combination thereof. A garment is provided that has at least one pocket. The pocket is adapted to receive the gas delivery pack. A nosepiece is provided that has at least one nose port. A single-sided modular medical cannula tubing assembly is provided that is operably attached to the nosepiece and the gas delivery pack for delivering a flow of gas from the gas delivery pack to the nosepiece. A single-sided modular cannula and a single-sided, hollow sleeve is provided. The sleeve at least partially encloses the nosepiece, allowing the single-sided modular medical nasal cannula to protrude through the nosepiece for a snug fit into the nostrils, and the single-sided modular cannula tubing assembly and is adapted to attach to an ear 66, a hat, helmet or an eyeglass frame of a user. A bracket is provided. The bracket is adapted to support a pair of headphones for use with a portable music system. The bracket is attached to the sleeve and locates the headphones in positions suitable for mounting the headphones to ears of a user.

(16) In still another variant, at least one clip is provided. The clip is adapted to secure the single-sided modular medical cannula tubing assembly to the garment.

(17) In yet another variant, the garment further includes a second pocket. The second pocket is adapted to secure a portable music system for connection to the headphones.

(18) In a further variant, a single-sided modular portable gas delivery system includes a gas delivery pack that has a gas storage region, a gas compression region, a gas filtration region or a combination thereof. A headpiece is provided that includes a sleeve that has a first end and a second end. A nosepiece is provided that is operably connected to the first end of the sleeve. The nosepiece that conceals a single-sided modular medical nasal cannula has at least one nose port.

A sleeve is provided that has a first and a second end. The first end is operably connected to the sleeve. The sleeve is formed to mount to a person's body. A single-sided modular cannula tubing assembly is provided that is operably attached to the second end of the tubular arm and the gas delivery pack. The gas delivery pack, single-sided modular cannula tubing assembly and headpiece are in fluid communication for delivering a flow of gas from the gas delivery pack to the nosepiece. A wireless transceiver adapted for use with a cellular telephone is provided. The transceiver has a listening portion 'and a speaking portion and is attached to the sleeve so as to position the listening portion adjacent a user's ear and the speaking portion adjacent a user's mouth.

(19) In still a further variant, the single-sided modular cannula tubing assembly includes a flow switch operably connected to switch the flow of gas on or off.

(20) In yet a further variant, a cushion is attached to the sleeve.

(21) In another variant of the invention, the sleeve is in fluid communication through a rotatable connector.

(22) In still another variant, the sleeve is adapted to mount to a human ear.

(23) In still another variant, the sleeve is designed to fold to fit a pocket and an elasticized string is connected to the frame and an interior surface of the pocket.

(24) In yet another variant, a single-sided modular portable gas delivery system includes a gas delivery pack that has a gas storage region, a gas compression region, a gas filtration region or a combination thereof. A headpiece is provided that includes a sleeve that has a first end and a second end. A nosepiece operably connected to the first end of the sleeve is provided. The nosepiece has at least one nose port. A sleeve tube is provided that has a first and a second end. The first end is operably connected to the sleeve. The sleeve is formed to mount to a person's body. A single-sided modular medical cannula tubing assembly is provided that is operably attached to the second end of the sleeve and the gas delivery pack. The gas delivery pack, single-sided modular cannula tubing assembly and headpiece are in fluid communication for delivering a flow of gas from the gas delivery pack to the nosepiece. A bracket is provided. The bracket is adapted to support a pair of headphones for use with a portable music system. The bracket is attached to the sleeve and locates the headphones in positions suitable for mounting the headphones to ears of a user.

(25) In still another variant, the single-sided modular cannula tubing assembly includes a flow switch operably connected to switch the flow of gas on or off.

(26) In a further variant, a cushion is attached to the sleeve.

(27) In still a further variant, the sleeve is in fluid communication through a rotatable connector.

(28) In yet a further variant, the sleeve is adapted to mount to a human ear.

(29) In another variant of the invention, the sleeve is designed to fold to fit a pocket and an elasticized string is connected to the sleeve and an interior surface of the pocket.

(30) In yet another variant, a single-sided modular portable gas delivery system includes a nosepiece and has at least one nose port. A gas delivery pack is provided that has a gas storage region, a gas compression region, a gas filtration region or a combination thereof. A single-sided modular cannula medical cannula tubing assembly is provided that is operably attached to the nosepiece that conceals the single-sided modular medical nasal cannula and the gas delivery pack for delivering gas from the gas delivery pack to the nosepiece. A single-sided modular cannula and a single-sided, hollow sleeve is provided. The sleeve at least partially encloses the nosepiece allowing the single-sided modular medical nasal cannula to protrude through the nosepiece for a snug fit into the nostrils and the single-sided modular cannula tubing assembly and is adapted to attach to an ear, a hat or an eyeglass frame of a user. A wireless transceiver adapted for use with a cellular telephone is provided. The transceiver has a listening portion and a speaking portion and is attached to the frame so as to position the listening portion adjacent a user's ear and the speaking portion adjacent a user's mouth.

(31) In a further variant, a single-sided modular portable gas delivery system includes a nosepiece and has at least one nose port. A gas delivery pack is provided that has a gas storage region, a gas compression region, a gas filtration region or a combination thereof. A single-sided modular cannula medical cannula tubing assembly is provided that is operably attached to the nosepiece that conceals the single-sided modular medical nasal cannula tubing and the gas delivery pack for delivering gas from the gas delivery pack to the nosepiece. A single-sided modular cannula and a single-sided, hollow sleeve is provided. The sleeve at least partially encloses the nosepiece allowing the medical nasal cannula to protrude through the nosepiece for a snug fit into the nostrils and the single-sided modular cannula tubing assembly and is adapted to attach to an ear, a hat or an eyeglass frame of a user. A bracket is provided. The bracket is adapted to support a pair of headphones for use with a portable music system. The bracket is attached to the sleeve and locates the headphones in positions suitable for mounting the headphones to ears of a user.

(32) In another variant, an air filtration mask is provided. The mask is removably attached to the hollow sleeve.

(33) In a yet another variant, an air filtration mask is provided. The mask is removably attached to the hollow sleeve.

(34) In still another variant, an accordion pleated section adjacent said nosepiece is provided. The pleated section provides adjustment of said nosepiece to said user's nostrils.

(35) In a final variant, an accordion pleated section adjacent said nosepiece is provided. The pleated section provides adjustment of said nosepiece to said user's nostrils.

Various objects, features, aspects, and advantages of the present invention will become more apparent from the following detailed description of preferred embodiments of the invention, along with the accompanying drawings in which like numerals represent like components.

BRIEF DESCRIPTION OF THE SEVERAL VIEWS OF THE DRAWING(S)

FIG. 9 is a perspective view of the FIG. 7 embodiment including a padded sleeve.

FIG. 10 is a perspective view of the FIG. 8 embodiment including a padded sleeve.

FIG. 12 is a perspective view of the FIG. 7 embodiment.

FIG. 13 is a perspective view of the FIG. 8 embodiment with stereo speakers.

FIG. 21B is a second perspective view of the modular mounting sleeve from

Figure 20A:
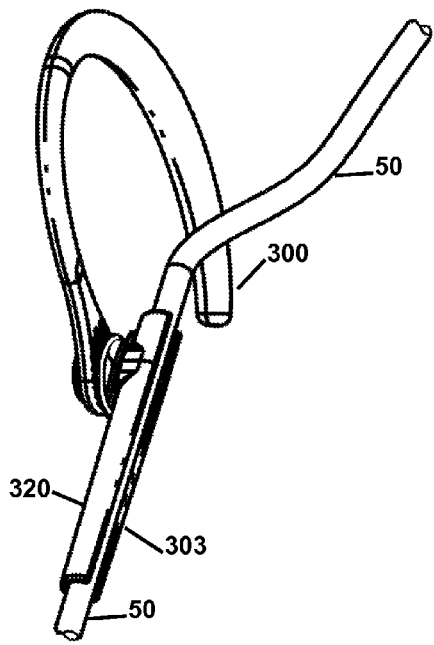
FIG. 20A is a first perspective view of the ear piece installed on a mounting sleeve.
Figure 20B:
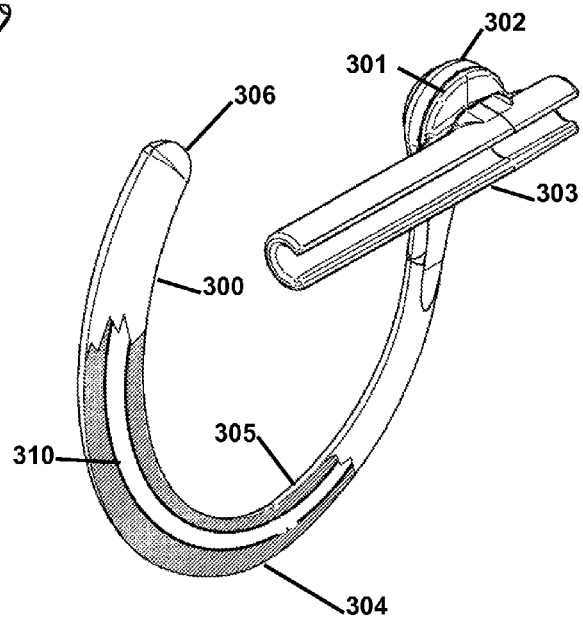
FIG. 20B is a second perspective view of the FIG. 20A embodiment

FIGS. 20A and 20B.

Figure 22:
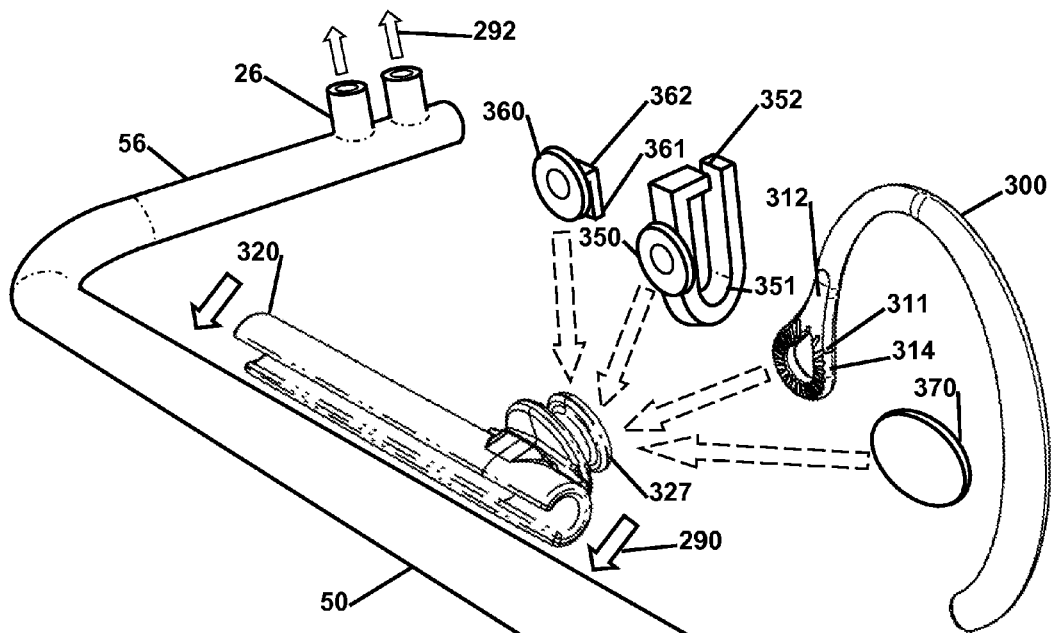

FIG. 22 is an exploded perspective view of the modular mounting sleeve from

Figure 21A:
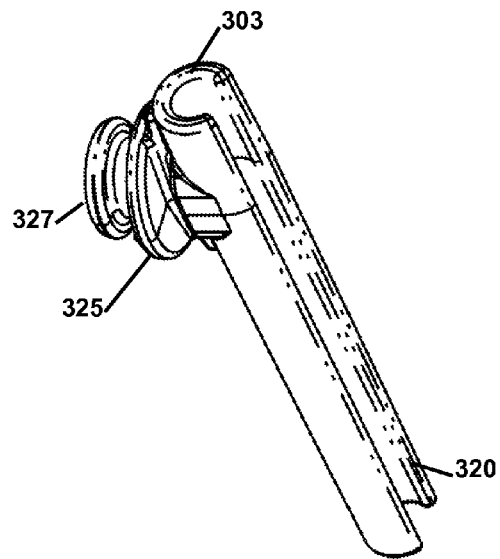
FIG. 21A is a first perspective view of the modular mounting sleeve from FIGS. 20A and 20B.
Figure 21B:
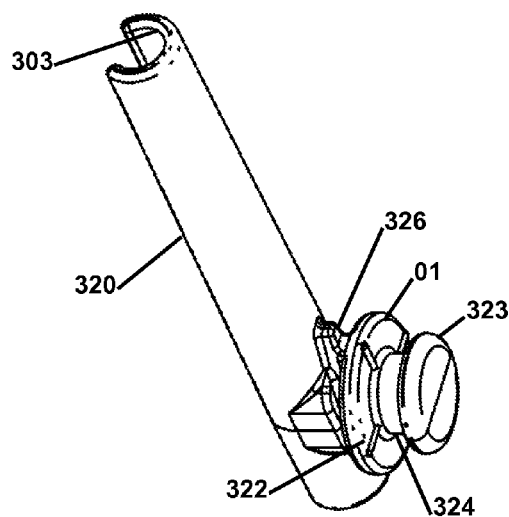

FIGS. 21A and 21B embodiment showing the modular mountable accessories.

Figure 23:
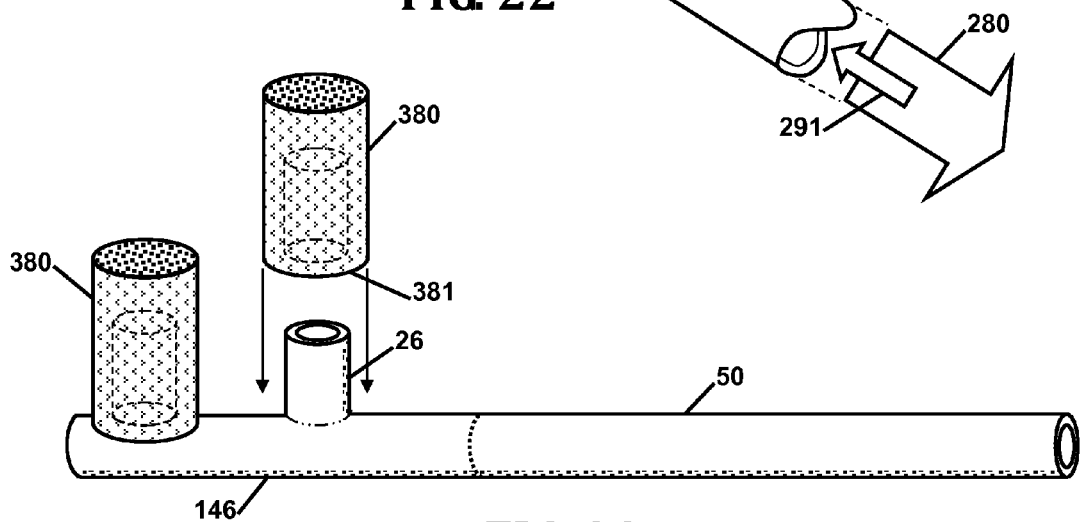

FIG. 23 is a perspective view of a Hepa Cannula Prong filters.

FIG. 24 is a front view of a Dual Air/O₂Pac.

FIG. 25 is a top view of the Dual Air/O₂Pac.

FIG. 26 is a front view of a storage holster for the Dual Air/O₂Pac.

Figure 1:
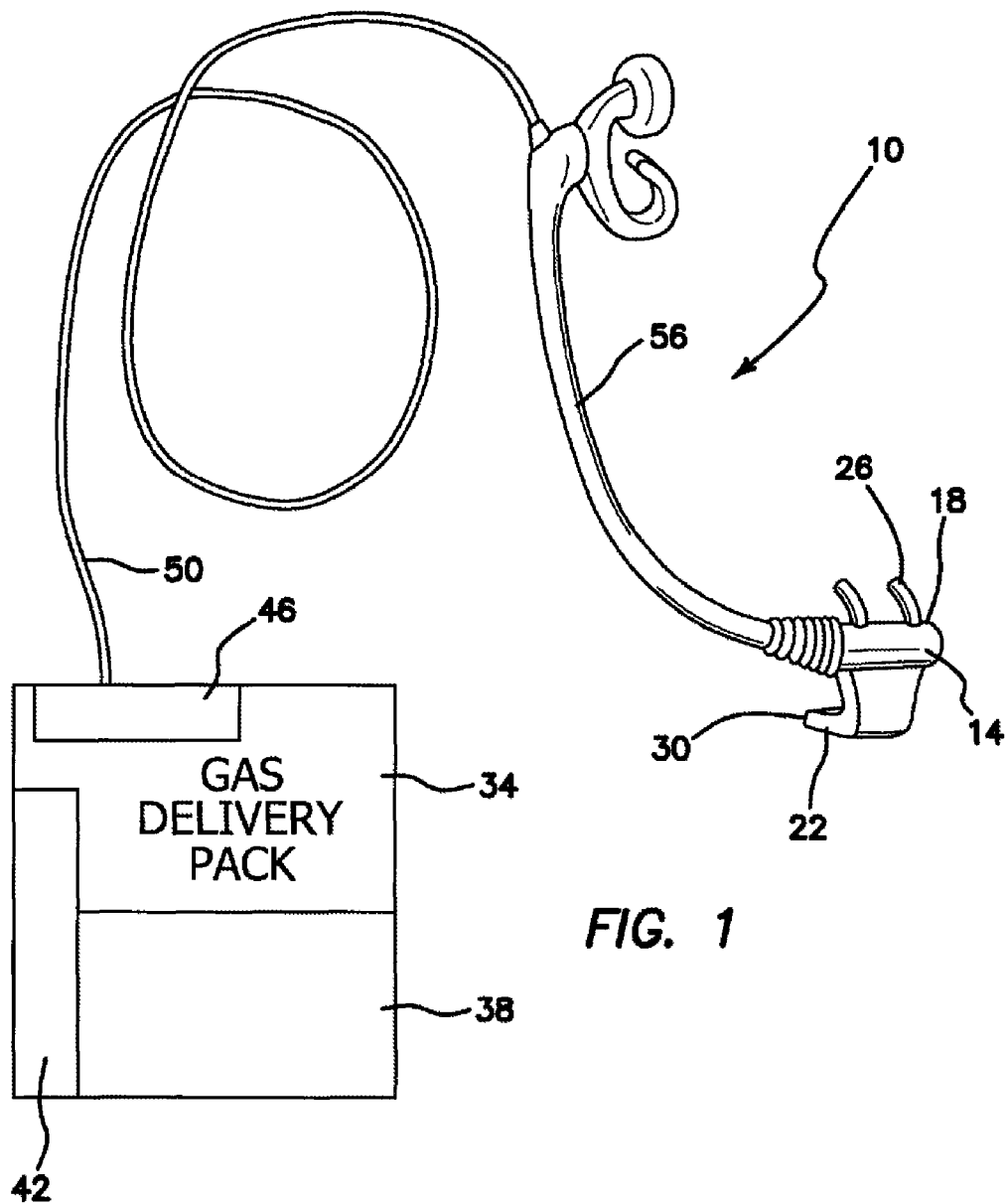
FIG. 1 is a perspective view of a single-sided modular oxygen and air delivery system having a mouthpiece with both nose and mouth breathing ports.
Figure 2:
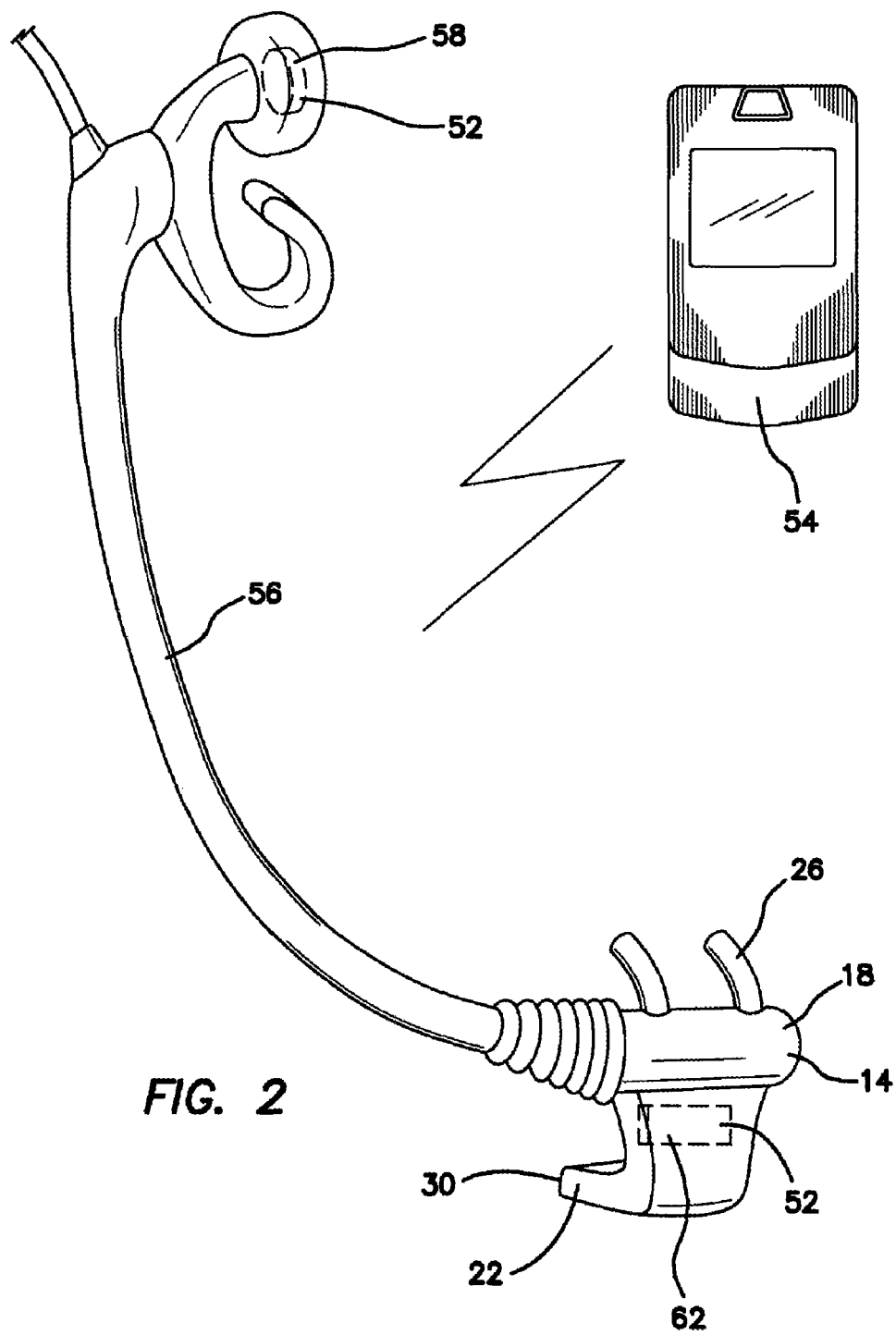
FIG. 2 is a perspective view of the FIG. 1 embodiment illustrating a wireless transceiver for a cellular telephone.

DETAILED DESCRIPTION OF THE INVENTION (1) FIGS. 1 and 2 illustrate a single-sided modular portable gas delivery system 10 that is constructed from the following components. A mouthpiece 14 is provided that has an upper region 18 and a lower region 22 extending from it. The upper region 18 includes at least one nose port 26 and the lower region 22 includes a mouth port 30. A gas delivery pack 34 is provided that has a gas storage region 38, a gas compression region 42, a gas filtration region 46 or a combination thereof. A single-sided modular medical cannula tubing assembly 50 is provided that is operably attached to the mouthpiece 14 and the gas delivery pack 34 for delivering gas from the gas delivery pack 24 to the mouthpiece 14. A single-sided modular cannula and a single-sided, hollow sleeve 56 is provided. The sleeve 56 at least partially encloses the mouthpiece 14 and single-sided modular cannula the tubing assembly 50 and is adapted to attach to an ear 66, a hat (not shown), helmet (not shown) or an eyeglass frame (not shown) of a user 134. A wireless transceiver 52 adapted for use with a cellular telephone 54 is provided. The transceiver 52 has a listening portion 58 and a speaking portion 62 and is attached to the sleeve 56 so as to position the listening portion 58 adjacent a user's ear 66 and the speaking portion 62 adjacent a user's mouth 70.

Figure 3:
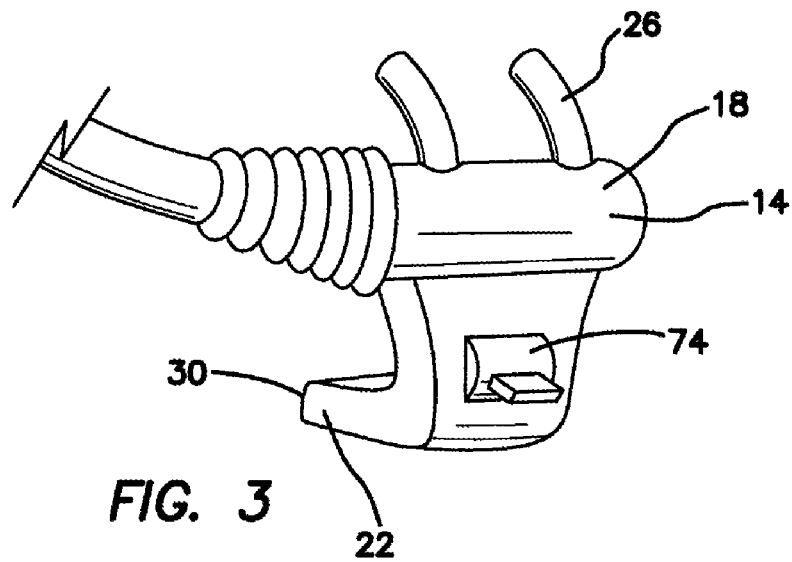
FIG. 3 is a close-up perspective view of the breathing ports illustrating a switch for controlling flow through the mouthpiece.

(2) In a variant of the invention, as illustrated in FIG. 3, the mouthpiece 14 includes a switch 74 for controlling flow of oxygen and air through the mouthpiece 14.

Figure 4:
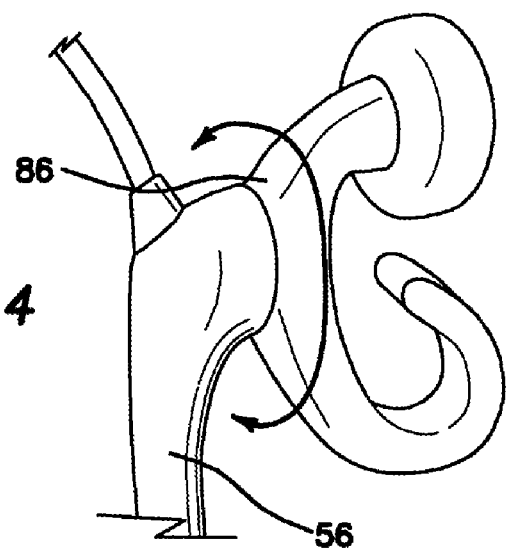
FIG. 4 is a close-up perspective view of an earpiece illustrating a swivel mounting.

(5) In yet another variant, as illustrated in FIG. 4, the sleeve 56 includes a least one rotatable connector 86 adjacent the listening portion 58.

Figure 5:
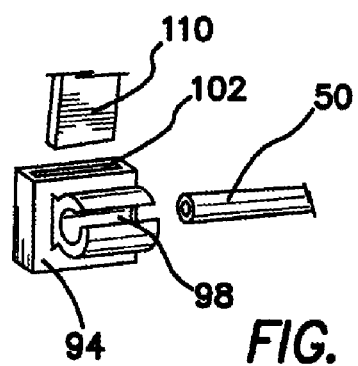
FIG. 5 is a perspective view of a clip for mounting to the single-sided modular cannula tubing assembly and a carrying strap for a gas delivery pack.

(6) In a further variant, as illustrated in FIG. 5, the single-sided modular portable gas delivery system includes at least one adapter 94 that has a first recess 98 and a second recess 102 formed in it. The first recess 98 is adapted to receive a portion 106 of the single-sided modular cannula tubing assembly 50 and the second recess 102 is adapted to receive a strap 110 for mounting the tubing assembly 50 with respect to a person's head 114.

Figure 6:
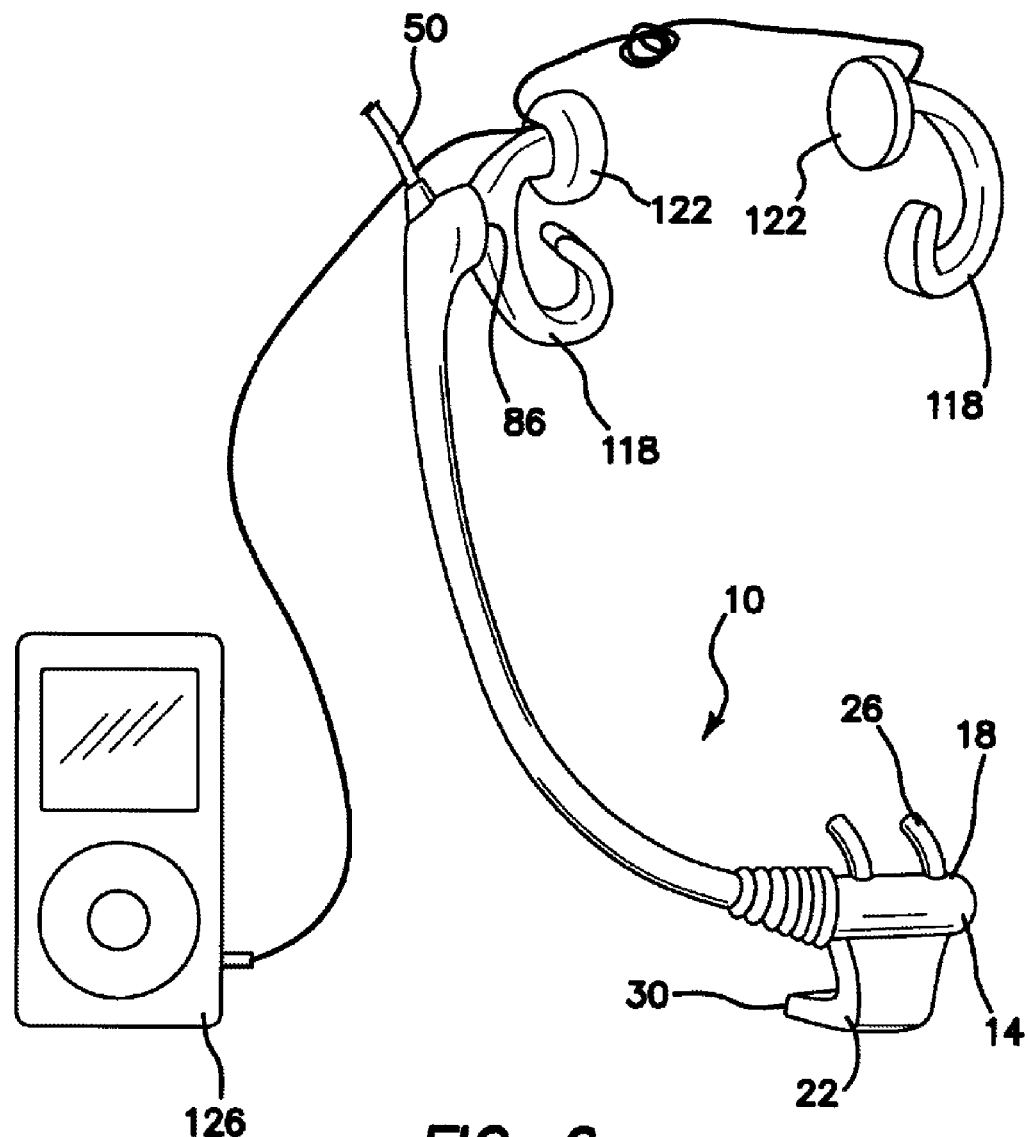
FIG. 6 is a perspective view of the FIG. 1 embodiment illustrating an integral personal music system.

(7) In still a further variant, as illustrated in FIG. 6, a single-sided modular portable gas delivery system 10 includes a mouthpiece 14 that has an upper region 18 and a lower region 22 extending from it. The upper region 18 includes at least one nose port 26 and the lower region 22 includes a mouth port 30. A gas delivery pack 34 is provided that has a gas storage region 38, a gas compression region 42, a gas filtration region 46 or a combination thereof. A single-sided modular cannula tubing assembly 50 is provided that is operably attached to the mouthpiece 14 and the gas delivery pack 34 for delivering gas from the gas delivery pack 34 to the mouthpiece 14. A single-sided modular cannula and a single-sided, hollow sleeve 56 is provided. The sleeve 56 at least partially encloses the mouthpiece 14 and the single sided modular cannula tubing assembly 50 and is adapted to attach to an ear 66, a hat, helmet or an eyeglass frame of a user 134. A bracket 118 is provided. The bracket 118 is adapted to support a pair of headphones 122 for use with a portable music system 126. The bracket 118 is attached to the sleeve 56 and locates the headphones 122 in positions suitable for mounting the headphones 122 to ears 66 of a user 134.

(8) In yet a further variant, as illustrated in FIG. 3, the mouthpiece 14 includes a switch 74 for controlling flow of oxygen and air through the mouthpiece 14.

(11) In yet another variant, the single-sided modular cannula tubing assembly 50 includes a least one rotatable connector 86 adjacent one of the headphones 122.

(12) In a further variant, as illustrated in FIG. 4, the single-sided modular cannula portable gas delivery system includes at least one adapter 94 that has a first recess 98 and a second recess 102 formed in it. The first recess 98 is adapted to receive a portion 106 of the single-sided modular cannula tubing assembly 50 and the second recess 102 is adapted to receive a strap 110 for mounting the single-sided modular cannula tubing assembly 50 with respect to a person's head 114.

Figure 7:
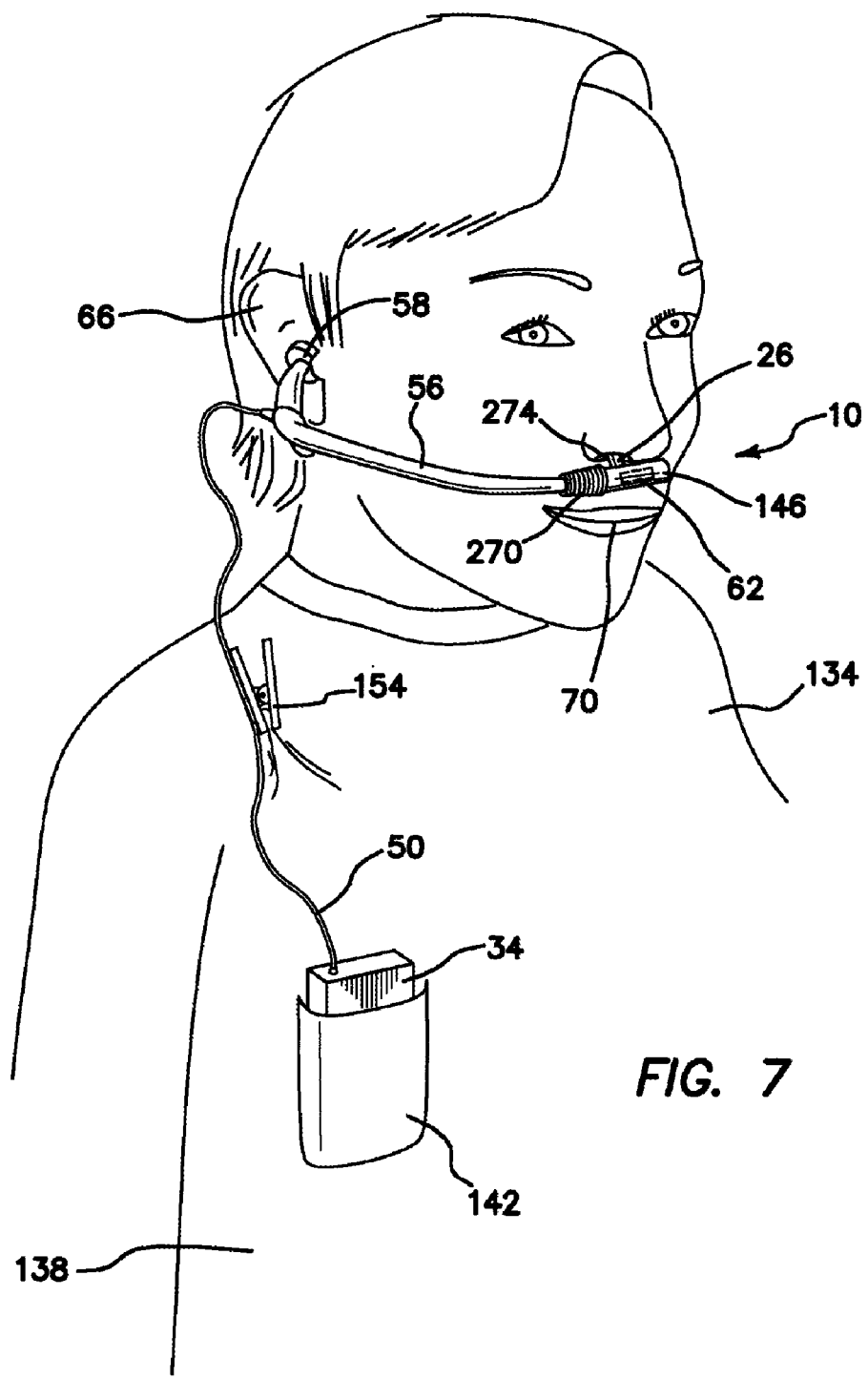
FIG. 7 is a perspective view of the FIG. 2 embodiment having only a nose port and attached to a user.

(13) In yet a further variant, as illustrated in FIG. 7, a single-sided modular portable gas delivery system includes a gas delivery pack 34 that has a gas storage region 38, a gas compression region 42, a gas filtration region 46 or a combination thereof. A garment 138 is provided that has at least one pocket 142, the pocket 142 is adapted to receive the gas delivery pack 34. A nosepiece 146 is provided that has at least one nose port 26. A single-sided modular medical cannula tubing assembly 50 is provided that is operably attached to the nosepiece, that conceals the single-sided modular medical nasal cannula 146, and the gas delivery pack 34 for delivering a flow of gas from the gas delivery pack 34 to the nosepiece 146. A single-sided modular cannula and a single-sided, hollow sleeve 56 is provided. The sleeve 56 at least partially encloses the nosepiece 146, allowing the single-sided modular medical nasal cannula 50 to protrude through the nosepiece 146, for a snug fit into the nostrils 274. The single-sided modular cannula tubing assembly 50 and is adapted to attach to an ear 66, a hat, helmet or an eyeglass frame of a user 134. A wireless transceiver adapted for use with a cellular telephone 54 is provided. The transceiver 54 has a listening portion 58 and a speaking portion 62 and is attached to the sleeve 56 so as to position the listening portion 58 adjacent a user's ear 66 and the speaking portion 62 adjacent a user's mouth 70.

(14) In still a further variant, at least one clip 154 is provided. The clip 154 is adapted to secure the single-sided modular medical cannula tubing assembly 50 to the garment 138.

Figure 8:
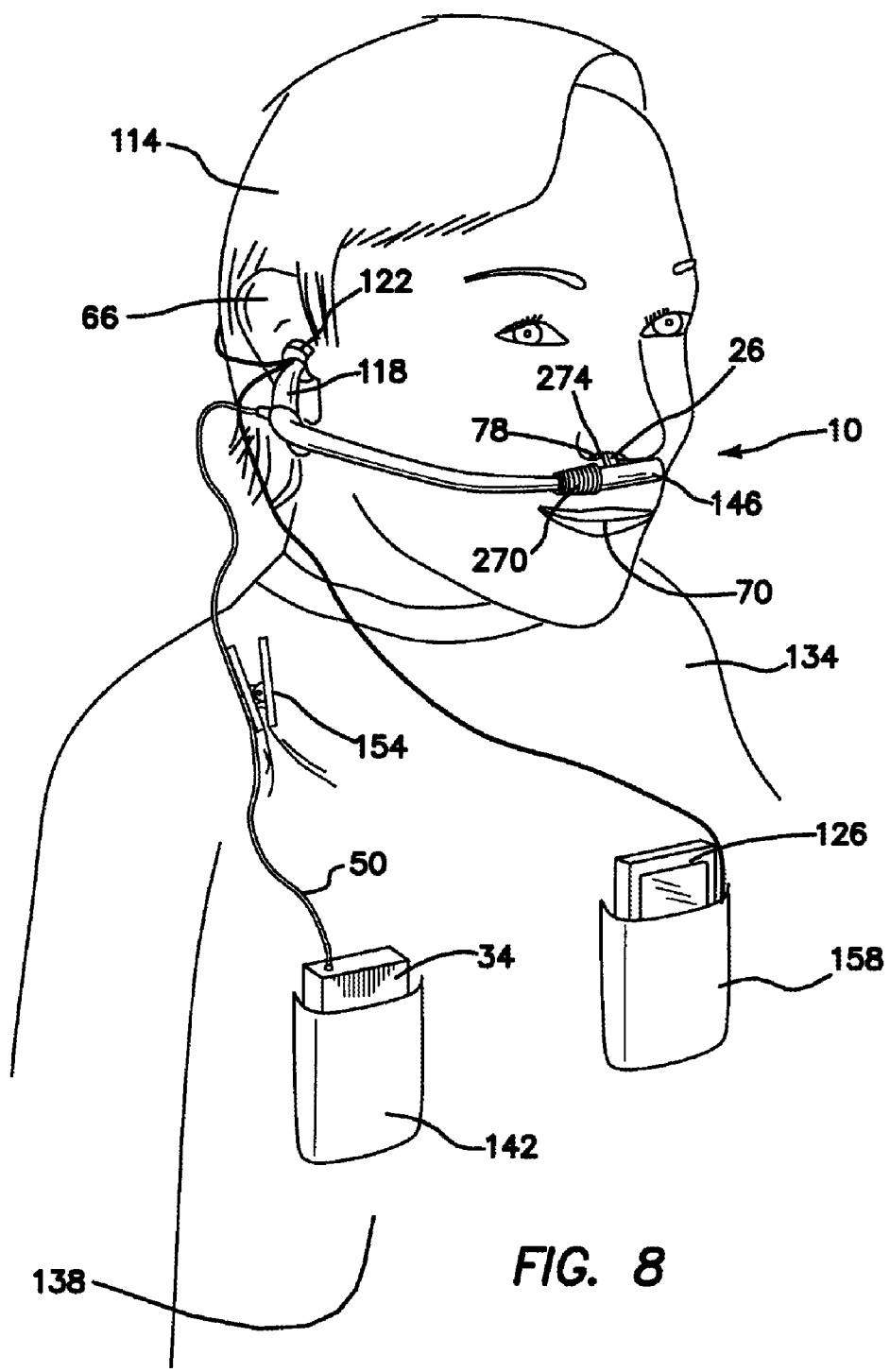
FIG. 8 is a perspective view of the FIG. 6 embodiment having only a nose port and attached to a user.

(15) In another variant of the invention, as illustrated in FIG. 8, a single-sided modular portable gas delivery system 10 includes a gas delivery pack 34 that has a gas storage region 38, a gas compression region 42, a gas filtration region 46 or a combination thereof. A garment 138 is provided that has at least one pocket 142. The pocket 142 is adapted to receive the gas delivery pack 34. A nosepiece 146 is provided that has at least one nose port 26. A single-sided modular medical cannula tubing assembly 50 is provided that is operably attached to the nosepiece 146 and the gas delivery pack 34 for delivering a flow of gas from the gas delivery pack 34 to the nosepiece 146. A single-sided modular cannula and a single-sided, hollow sleeve 56 is provided. The sleeve 56 at least partially encloses the nosepiece, allowing the single-sided modular medical nasal cannula 50 to protrude through the nosepiece 146 for a snug fit into the nostrils 274, and the single-sided modular cannula tubing assembly 50 and is adapted to attach to an ear 66, a hat, helmet or an eyeglass frame of a user 134. A bracket 118 is provided. The bracket 118 is adapted to support a pair of headphones 122 for use with a portable music system 126. The bracket 118 is attached to the sleeve 56 and locates the headphones 122 in positions suitable for mounting the headphones 122 to ears 66 of a user 134.

(16) In still another variant, at least one clip 154 is provided. The clip 154 is adapted to secure the single-sided modular medical cannula tubing assembly 50 to the garment 138.

(17) In yet another variant, the garment 138 further includes a second pocket 158. The second pocket 158 is adapted to secure a portable music system 126 for connection to the headphones 122.

Figure 14:
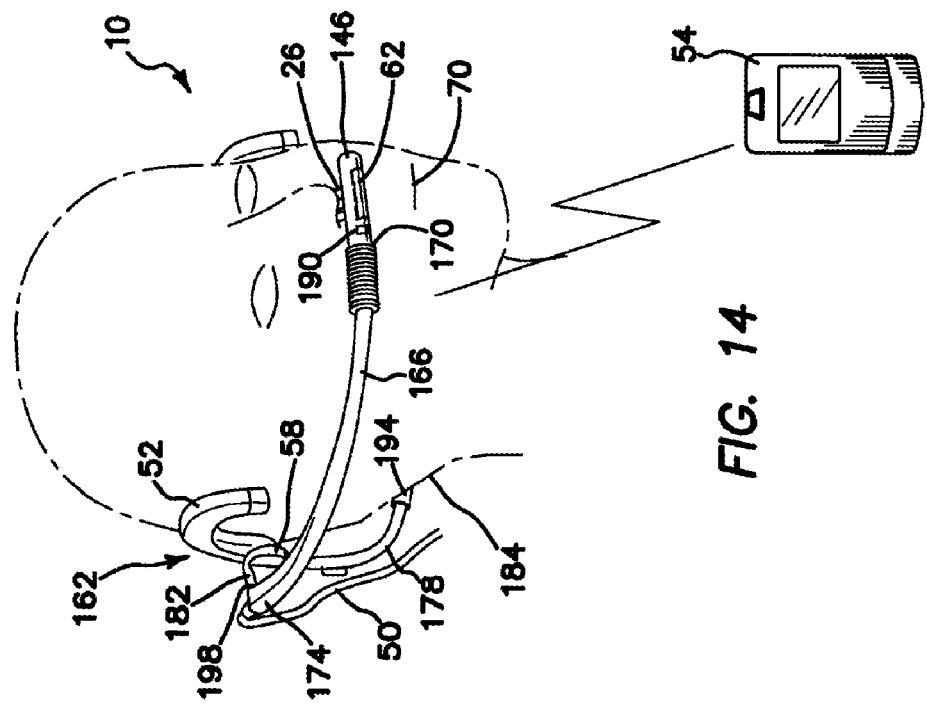
FIG. 14 is a perspective view of another embodiment including a sleeve resting on the neck of the user and a wireless transceiver for a cellular telephone.
Figure 16:
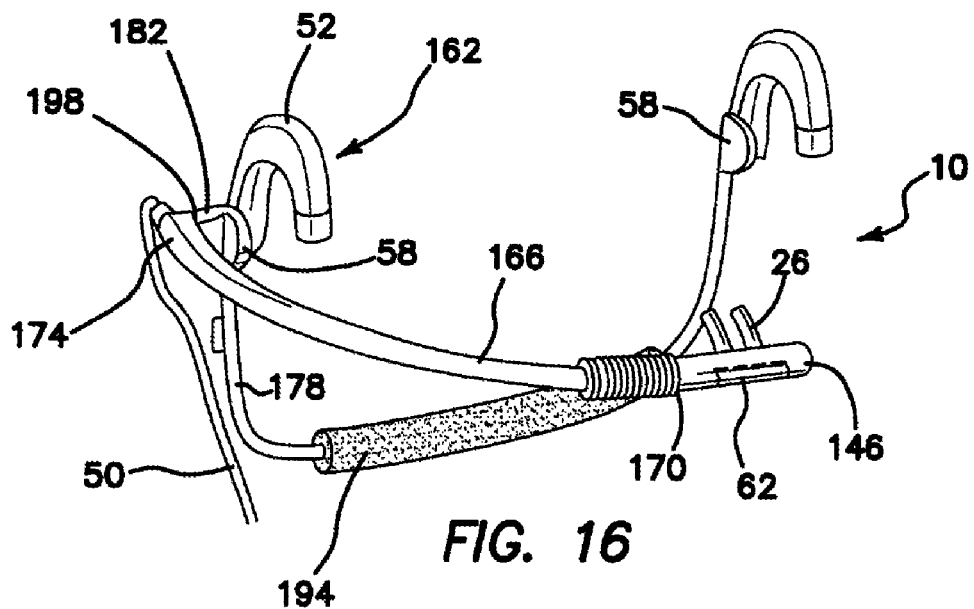
FIG. 16 is a perspective view of the FIG. 14 embodiment showing a padded section on the sleeve.

(18) In a further variant, as illustrated in FIGS. 14 and 16, a single-sided modular portable gas delivery system 10 includes a gas delivery pack 34 that has a gas storage region 38, a gas compression region 42, a gas filtration region 46 or a combination thereof. A headpiece 162 is provided that includes a sleeve 166 that has a first end 170 and a second end 174. A nosepiece 146 is provided that is operably connected to the first end 170 of the sleeve 166. The nosepiece 146 that conceals a single-sided modular medical nasal cannula has at least one nose port 26. The sleeve 178 is provided that has a first 182 and a second 186 end. The first end 182 is operably connected to the sleeve 166. The sleeve 178 is formed to mount to a person's body 184. A single-sided modular cannula tubing assembly 50 is provided that is operably attached to the second end 174 of the sleeve 166 and the gas delivery pack 34. The gas delivery pack 34, single-sided modular cannula tubing assembly 50 and headpiece 162 are in fluid communication for delivering a flow of gas from the gas delivery pack 34 to the nosepiece 146. A wireless transceiver 52 adapted for use with a cellular telephone 54 is optimally provided. The transceiver 52 has a listening portion 58 and a speaking portion 62 and is attached to the sleeve 166 so as to position the listening portion 58 adjacent a user's ear 66 and the speaking portion adjacent a user's mouth 70.

(19) In still a further variant, as illustrated in FIGS. 9, 12 and 14, the single-sided modular cannula tubing assembly 50 includes a flow switch 190 operably connected to switch the flow of gas on or off.

(20) In yet a further variant, as illustrated in FIGS. 14 and 16, a cushion 194 is attached to the sleeve 178.

(21) In another variant of the invention, the sleeve 178 and the sleeve 166 are in fluid communication through a rotatable connector 198.

(22) In still another variant, the sleeve 178 is adapted to mount to a human ear 66.

Figure 11:
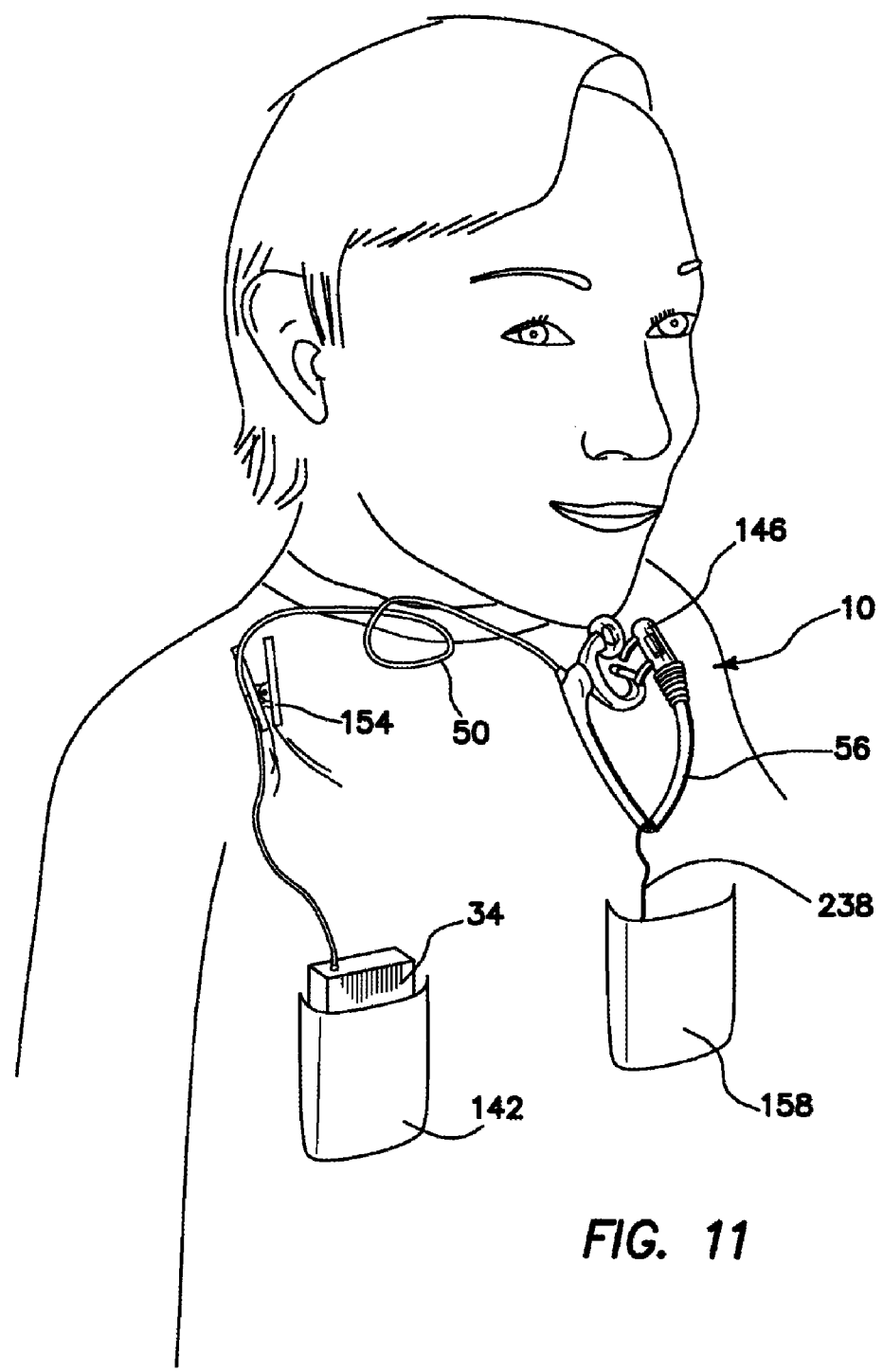
FIG. 11 is a perspective view of the FIG. 7 embodiment including a foldable frame attached to a user's garment.

(23) In still another variant, as illustrated in FIG. 11, the sleeve 56 is designed to fold to fit a pocket 158 and an elasticized string 238 is connected to the sleeve 56 and an interior surface 234 of the pocket 158.

Figure 15:
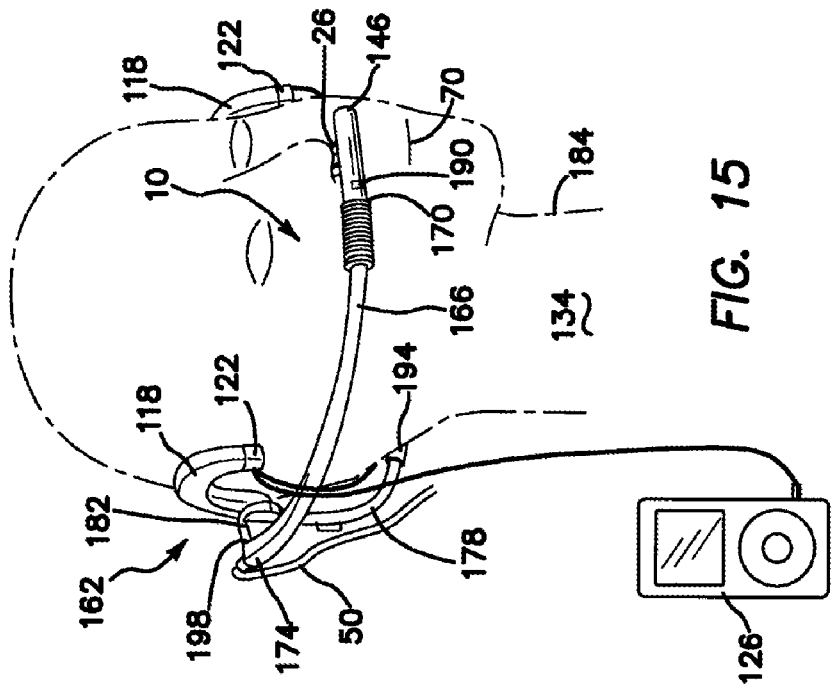
FIG. 15 is a perspective view of another embodiment including a sleeve resting on the neck of the user and an integral personal music system.
Figure 17:
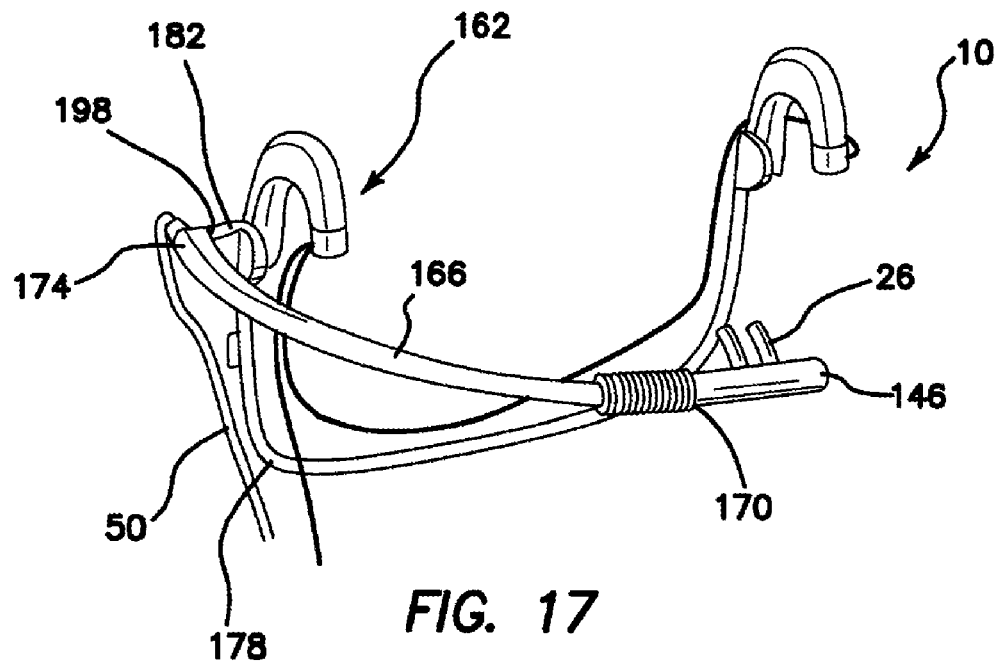
FIG. 17 is a perspective view of the FIG. 15 embodiment.

(24) In yet another variant, as illustrated in FIGS. 15 and 17, a single-sided modular portable gas delivery system 10 includes a gas delivery pack 34 that has a gas storage region 38, a gas compression region 42, a gas filtration region 46 or a combination thereof. A headpiece 162 is provided that includes a sleeve 166 that has a first end 170 and a second end 174. A nosepiece 146 that conceals a single-sided modular cannula medical nasal cannula is provided that is operably connected to the first end 170 of the sleeve 166. The nosepiece 146 has at least one nose port 26. The sleeve 178 is provided that has a first 182 and a second 186 end. The first end 182 is operably connected to the sleeve 166. The sleeve 178 is formed to mount to a person's body 184. A single-sided modular medical cannula tubing assembly 50 is provided that is operably attached to the second end 174 of the sleeve. 166 and the gas delivery pack 34. The gas delivery pack 34, single-sided modular medical cannula tubing assembly 50 and headpiece 162 are in fluid communication for delivering a flow of gas from the gas delivery pack 34 to the nosepiece 146, allowing the medical single sided modular nasal cannula 50 to protrude through the nosepiece 146 for a snug fit into the nostrils 274. A bracket 118 is provided. The bracket 118 is adapted to support a pair of headphones 122 for use with a portable music system 126. The bracket 118 is attached to the sleeve 178 and locates the headphones 122 in positions suitable for mounting the headphones 122 to ears 66 of a user 134.

(25) In still another variant, the single-sided modular cannula tubing assembly 50 includes a flow switch 190 operably connected to switch the flow of gas on or off.

(26) In a further variant, a cushion 194 is attached to the sleeve.

(27) In still a further variant, the sleeve 178 is in fluid communication through a rotatable connector 198.

(28) In yet a further variant, the sleeve 178 is adapted to mount to a human ear 66.

(29) In still another variant, as illustrated in FIG. 11, the sleeve 56 is designed to fold to fit a pocket 158 and an elasticized string 238 is connected to the sleeve 56 and an interior surface 234 of the pocket 158.

(30) In yet another variant, as illustrated in FIGS. 9 and 12, a single-sided modular portable gas delivery system 10 includes a nosepiece 146 that has at least one nose port 26. A gas delivery pack 34 is provided that has a gas storage region 38, a gas compression region 42, a gas filtration region 46 or a combination thereof. A single-sided modular medical cannula tubing assembly 50 is provided that is operably attached to the nosepiece 146 that conceals the single-sided modular medical nasal cannula tubing 50 and the gas delivery pack 34 for delivering gas from the gas delivery pack 34 to the nosepiece 146. A single-sided modular cannula and a single-sided, hollow sleeve 56 is provided. The sleeve 56 at least partially encloses the nosepiece, allowing the single-sided modular medical nasal cannula to protrude through the nosepiece 146 for a snug fit into the nostrils, and the single-sided modular cannula tubing assembly 50 and is adapted to attach to an ear 66, a hat, helmet or an eyeglass frame of a user 134. A wireless transceiver 52 adapted for use with a cellular telephone 54 is provided. The transceiver 52 has a listening portion 58 and a speaking portion 62 and is attached to the sleeve 56 so as to position the listening portion 58 adjacent a user's ear 66 and the speaking portion adjacent a user's mouth 70.

(31) In a further variant, as illustrated in FIGS. 10 and 13, a single-sided modular portable gas delivery system 10 includes a nosepiece 146 that has at least one nose port 26. A gas delivery pack 34 is provided that has a gas storage region 38, a gas compression region 42, a gas filtration region 46 or a combination thereof. A single-sided modular medical cannula tubing assembly 50 is provided that is operably attached to the nosepiece 146 that conceals the single-sided modular medical nasal cannula tubing 50, and the gas delivery pack 34 for delivering gas from the gas delivery pack 34 to the nosepiece 146. A single-sided modular cannula and a single-sided, hollow sleeve 56 is provided. The sleeve 56 at least partially encloses the nosepiece allowing the single-sided modular medical nasal cannula to protrude through the nosepiece 146 for a snug fit into the nostrils 274 and the single-sided modular cannula tubing assembly 50 and is adapted to attach to an ear 66, a hat, helmet or an eyeglass frame of a user. A bracket 118 is provided. The bracket 118 is adapted to support a pair of headphones 122 for use with a portable music system 126. The bracket 118 is attached to the sleeve 56 and locates the headphones 122 in positions suitable for mounting the headphones 122 to ears 66 of a user 134.

Figure 18:
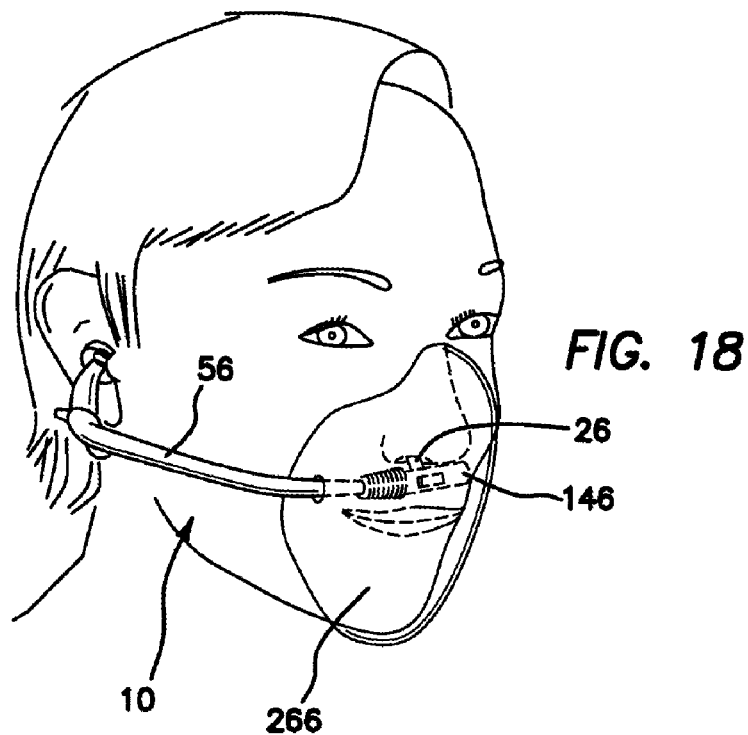
FIG. 18 is a perspective view of the FIG. 7 embodiment including a face mask.
Figure 19:
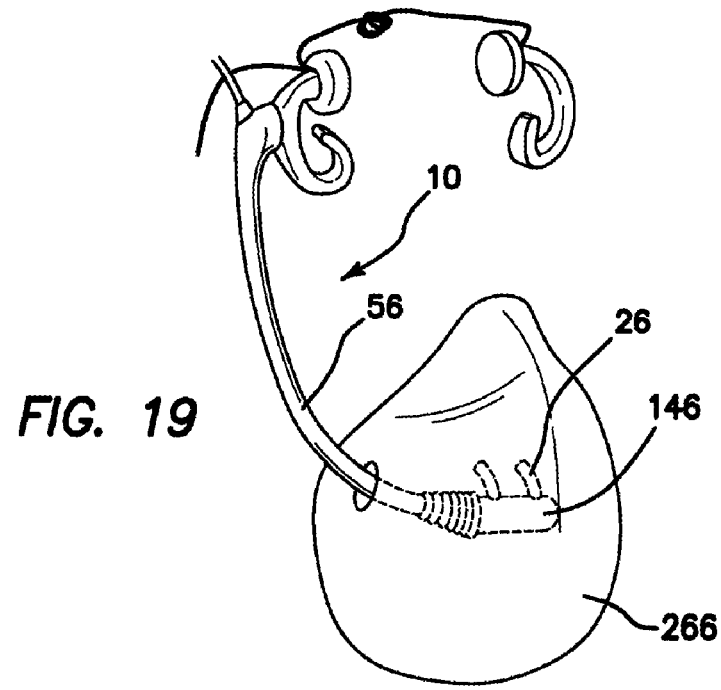
FIG. 19 is a perspective view of the FIG. 8 embodiment including a face mask.

(32) In another variant, as illustrated in FIGS. 18 and 19, an air filtration mask 266 is provided. The mask 266 is removably attached to the hollow sleeve 56.

(33) In still another variant, an air filtration mask 266 is provided. The mask 266 is removably attached to the hollow frame 56.

(34) In still another variant, as illustrated in FIGS. 7, 9 and 12, an accordion pleated section 270 adjacent said nosepiece 146 is provided. The pleated section 270 provides adjustment of said nosepiece 146 to said user's nostrils 274.

(35) In a final variant, an accordion pleated section 270 as illustrated in FIGS. 8, 10 and 13; adjacent said nosepiece 146 is provided. The pleated section 270 provides adjustment of said nosepiece 146 to said user's nostrils 274

In another preferred embodiment, FIGS. 20A and 20B show a first and a second perspective view of the ear piece installed on a modular mounting sleeve and FIGS. 21A and 21B show a first and a second perspective view of the modular mounting sleeve from FIGS. 20A and 20B. The single-sided modular gas delivery system in this embodiment uses a modular mounting sleeve 320 having an elongated central semi-circular cavity 303. The modular mounting sleeve 320 has a backing 326 comprising an enlarged disc 325 that is perpendicular to the central semi-circular cavity 303 and connected to the modular mounting sleeve 320 at first face of the enlarged disc 325. The first enlarged disc 325 further has a hub 324 that extends from the enlarged disk 325 at a second side that is essential concentric to the first face. A second enlarged disc 327 that is connected to the hub 324 that is larger than said hub 324 but smaller than the first enlarged disk 325. The first 325 and or the second enlarged disc 327 further have a plurality of elevated ridges 322.

An ear hanger 300 having a semi-circular resilient sleeve 305. The ear piece 300 has an opening 314 (shown in FIG. 22) that engages onto said hub 324 between the first 325 and the second 327 enlarged discs, and the 314 opening having a plurality of recesses 311 (shown in FIG. 22) that engage into the plurality of elevated ridges 322 to temporally engage said ear piece 300 on the hub 324 in at least two unique locations. The ear piece 300 is at least partially flattened 301 to 302 in the area of the opening to fit within the first 325 and the second 327 enlarged discs. The ear piece 300 further has a metal insert 310 that is located at least partially within the ear piece 300. The metal insert 310 can be formed from flat sheet material or can be formed from wire. The metal insert 310 is malleable or and allows the ear piece 300 to be bent, shaped and retain the shape for the comfort of the user.

The ear piece is formed from a flexible resilient material that allows the ear piece to be shaped to conform to a user with an inside diameter 305 and an outside diameter 304. The free end of the ear piece 300 has a rounded end 306. The outer end 323 of the second enlarged disk 327 allows for the ear piece opening 314 to removable pass over the second enlarged disk 327.

FIG. 22 is an exploded perspective view of the modular mounting sleeve from FIGS. 21A and 21B that shows an embodiment showing the mountable accessories. The modular mounting sleeve 320 is shown with the semi-circular opening that allows the modular mounting sleeve 320 to be removably secured 290 to a single-sided modular medical cannula tubing assembly 50 is provided that is operably attached to the single-sided modular nasal cannula 26 through which the oxygen and or Hepa filtered air is delivered to 291 entering the single-sided modular cannula tubing 50 and out 292 of the nasal cannula 26. The single-sided modular cannula tubing 50 is connected 280 to an oxygen and or a Hepa filtered air supply.

The interchangeable accessories include, but are not limited to an adapter 360 for mounting on eye glasses. The adapter 360 has an extension 362 with an arm 361 for mounting onto the frames of eye glasses. A hat adapter 350 allows for mounting onto a hat or helmet from either mounting from the bottom up of from the top down, depending upon desired orientation. This adapter 350 has an open flexible spring 351 with a pinch area 352 for gripping the hat or helmet. The ear piece 300 was previously described herein, but in this figure the flattened area 312 is visible with the recesses 311 around the opening 314 that engage into the elevated ridges 322, shown in FIGS. 21A and 21B. An adhesive backed button 370 can also be temporally secured to the mounting modular sleeve 320.

FIG. 23 is a perspective view of a Hepa cannula prongs. This figure shows a tubing assembly 50 connected to a nose piece 146. The nose piece 146 has a plurality of nose ports 26. The nose ports 26 are configured to accept Hepa prong filters 380. The Hepa prong filters are configured to fit and seal the nostrils of a user to filter out ambient harmful air from coming into breathing and allows for comfortable exhaling. The bottom 381 is sealed to reduce or prevent the user from drawing ambient air through the bottom of the Hepa prong filters 380. Hepa filters may also provide aroma's and or vitamins in their essential oil state, or may be saturated within the Hepa filters. The Hepa filters may also include medicine for absorption through inhaling thereby avoiding the waste from digestion.

FIG. 24 is a front view of a Dual Air/$O_2$Pac and FIG. 25 is a top view of the Dual Air/$O_2$Pac. The Dual Air/$O_2$ Pac is a self-contained unit for supplying air or $O_2$. The Dual air/$O_2$ Pac comprise an outer casing 400, and in the embodiment shown the outer casing is curved to better conform around a body part. Internally the dial air/$O_2$ Pac have separate containers for Air 430 & 431 and $O_2$ 432 & 433. Volume gauges 401 & 402 on the outside of the housing displays 401 & 402 the remaining pressure, volume or time remaining in the tanks.

The containers are connected 434 through a switch 410 that allows for the filtered air or the $O_2$ to flow out of the top of the dual air/$O_2$ Pac. The switch 411 is a three-way switch 410 that is user switchable from off to flowing air or to flowing $O_2$. The front of the housing 400 further may include an area for a logo 403. A connector 404 connects 405 the single-sided modular medical cannula tubing assembly 50 to a respirator flow switch 420 to open 421 or close flow out of the remainder of the single-sided modular medical cannula tubing assembly 50. The dual air/$O_2$ Pac has four tanks that can be configured with any quantity of each type of gas disclosed or other types of gas including but not limit to helium, nitrogen or custom blends.

FIG. 26 is a front view of a storage holster for the Dual Air/$O_2$ Pac. The storage holster is made of sturdy swimsuit/scuba fabric that can be selected to match the bathing suit of the user. A retractable tubing 461 & 462. One or more floats 451 can be used to prevent the belt from sinking in water. The elastic strap 450 is securable with hook 452 and loop 453 fasteners or magnetic fasteners to retain the elastic strap 450 on an arm or other extremity of a user. The single-sided modular medical cannula tubing assembly 50 connects from the dual air/$O_2$ Pac to the retractable tubing 462. The retractable tubing is a semi-rigid accordion type tubing with built-in folds with an elastic string that self-collapses when released. The dual air/$O_2$ Pac is useful for occasional or emergency air use, such as for a surfer when the surfer wipes out and loses vertical orientation. Under these conditions a user can simply pull out the mouthpiece 460 and bite down to begin the flow of air or $O_2$ into the mouthpiece 460. The dual air/$O_2$ Pac housing 400 is retained within a case 454 that is secured with a strap 455.

Thus, specific embodiments of a gas delivery system have been disclosed. It should be apparent, however, to those skilled in the art that many more modifications besides those described are possible without departing from the inventive concepts herein. The inventive subject matter, therefore, is not to be restricted except in the spirit of the appended claims.

The invention claimed is:

1. A single-sided modular cannula and gas delivery system's modular sleeve comprising:
   a modular mounting sleeve having an elongated central semi-circular cavity;
   said modular mounting sleeve having a backing comprising a first enlarged disc that is perpendicular to said central semi-circular cavity and connected to said modular mounting sleeve at first face of said first enlarged disc;
   said first enlarged disc further having a hub that extends from said first enlarged disk at a second side that is essentially concentric to said first face;
   a second enlarged disc that is connected to said hub that is larger than said hub, but smaller than said first enlarged disc;
   said first enlarged disc and/or said second enlarged disc further having a plurality of elevated ridges;
   an ear hanger having a semi-circular resilient modular sleeve;
   said ear hanger having an opening that engages onto said hub between said first and said second enlarged discs, and
   said opening having a plurality of recesses that engage into said plurality of elevated ridges to temporally engage said ear hanger on said hub in at least two unique locations.

2. The single-sided modular cannula and gas delivery system's modular sleeve according to claim 1 wherein said ear hanger is flattened in an area of said opening.

3. The single-sided modular cannula and gas delivery system's modular sleeve according to claim 1 wherein said ear hanger further has a malleable insert that is located at least partially within said ear hanger.

4. The single-sided modular cannula and gas delivery system's modular sleeve according to claim 1 wherein said ear hanger is formed from a flexible resilient material.

5. The single-sided modular cannula and gas delivery system's modular sleeve according to claim 1 wherein a free end of said ear hanger has a rounded end.

6. The single-sided modular cannula and gas delivery system's modular sleeve according to claim 1 said second enlarged disc allows for said opening in said ear hanger to pass over said second enlarged disc to allow for said ear hanger to be engaged onto said mounting sleeve.

7. The single-sided modular cannula and gas delivery system's modular sleeve according to claim 1 wherein said ear hanger is rotatable around said mounting sleeve on said hub.

8. The single-sided modular cannula and gas delivery system's modular sleeve according to claim 1 wherein there is at least four of said plurality of elevated ridges.

9. The single-sided modular cannula and gas delivery system's modular sleeve according to claim 1 wherein said central semi-circular cavity is sized for engagement onto a personal oxygen supply hose.

10. The single-sided modular cannula and gas delivery system's modular sleeve according to claim 9 wherein said modular mounting sleeve is repositionable on said personal oxygen supply hose.

* * * * *